(12) United States Patent
Gilli

(10) Patent No.: US 8,490,791 B2
(45) Date of Patent: Jul. 23, 2013

(54) KIT AND METHOD FOR PROTECTING AT LEAST ONE OF DRESSINGS AND WOUNDED SKIN REGIONS OF THE BODY

(76) Inventor: Eric Gilli, Cassis (FR)

( * ) Notice: Subject to any disclaimer, the term of this patent is extended or adjusted under 35 U.S.C. 154(b) by 0 days.

(21) Appl. No.: 11/817,497

(22) PCT Filed: Mar. 22, 2006

(86) PCT No.: PCT/FR2006/000627
§ 371 (c)(1),
(2), (4) Date: Oct. 12, 2007

(87) PCT Pub. No.: WO2006/100382
PCT Pub. Date: Sep. 28, 2006

(65) Prior Publication Data
US 2008/0179213 A1    Jul. 31, 2008

(30) Foreign Application Priority Data
Mar. 23, 2005  (FR) ...................... 05 02847

(51) Int. Cl.
*A61B 19/02*  (2006.01)
*A61L 15/10*  (2006.01)
*B65D 85/00*  (2006.01)

(52) U.S. Cl.
USPC .............................. 206/440; 206/570; 602/41

(58) Field of Classification Search
USPC .......... 206/438–441, 570–572; 401/132–133; 602/41
See application file for complete search history.

(56) References Cited

U.S. PATENT DOCUMENTS

| | | | |
|---|---|---|---|
| 2,649,199 A * | 8/1953 | Werman | 206/440 |
| 4,022,203 A * | 5/1977 | Ackley | 206/440 |
| 5,000,172 A * | 3/1991 | Ward | 206/441 |
| 5,599,290 A | 2/1997 | Hayes et al. | |
| 6,087,549 A * | 7/2000 | Flick | 602/41 |
| 6,412,639 B1 * | 7/2002 | Hickey | 206/570 |
| 6,547,467 B2 * | 4/2003 | Quintero | 206/438 |
| 7,306,390 B2 * | 12/2007 | Quintero et al. | 401/133 |
| 7,331,463 B2 * | 2/2008 | Hickey | 206/570 |
| 7,398,883 B2 * | 7/2008 | Tucker | 206/570 |
| 2003/0212358 A1 | 11/2003 | Cavanagh et al. | |

FOREIGN PATENT DOCUMENTS

WO    WO 94/23677    10/1994

* cited by examiner

*Primary Examiner* — Bryon Gehman
(74) *Attorney, Agent, or Firm* — Greenblum & Bernstein, P.L.C.

(57) ABSTRACT

The invention concerns a kit for protecting dressings and/or traumatized skin regions of the body. The kit includes a case containing at least one non-dedicated flexible and water-impermeable base sheet or global sheet with dimensions enabling a plurality of single or individual adapted covering parts to be cut out. The base sheet is preferably made of a non-allergenic material and easily divisible into pieces or fractions of smaller dimensions, for example with a pair of scissors. The kit also includes a package containing a water-impermeable and non-allergenic pasty adhesive, having properties enabling adherence both to the skin and to the protective sheet.

23 Claims, 3 Drawing Sheets

KIT AND METHOD FOR PROTECTING AT LEAST ONE OF DRESSINGS AND WOUNDED SKIN REGIONS OF THE BODY

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

This invention concerns a method for protecting dressings and/or wounded skin regions of the body. It also concerns a protection kit to be used for the application of this method.

2. Description of Related Art Including Information Disclosed Under 37 CFR 1.97 and 37 CFR 1.98.

Various devices have been offered to this day to ensure the protection of dressings applied to wounded skin areas of the body or directly on these areas in order to prevent these dressings or wounds from becoming wet or soiled by splashes of water or other contaminated fluids. For example, these devices are intended for persons wearing any dressings so they can bathe or take a shower without needing to worry about them getting wet.

The devices of the state of the art consist of soft, dedicated sheets, generally of rectangular shape (WO-89/03765, WO-99/02110), or of sheaths (WO-91/17733, WO-94/24971, FR-2 706 290), or of sleeves (EP-0 358 451, WO-93/14730, FR-2 686 786) provided with permanent and original means to allow their removable attachment to the areas to be protected.

A common inconvenience of all these devices that is especially of concern to individuals, is due to the fact that the dimensions, shapes and locations of the surfaces that are covered by the dressings or of the lesions, are unforeseeable and highly variable. Potential users wind up purchasing and keeping a wide range of sizes of protection devices in order to cover a significant range of surfaces. The result is that the purchaser will be in the possession of a certain number of items that are either too small or too large that will never be used or which will have to be discarded after a certain period of conservation. Furthermore, the shape of these items is not adaptable to the shape of the dressings or to that of the traumatized skin areas that need to be protected, the effect being that the shape can be a source of hindrance of movement of the limb or the part of the body covered by the dressing.

In order to solve another problem, one is familiar (WO-94/23677) with a thermal blanket that can be used to prevent a heat loss of the parts of the human or animal body, consisting of a reflective metal foil or a metallized plastic film provided with perforations to allow gas exchanges and attached to the skin by means of an adhesive tape, preferably double-sided, and also provided with perforations. Such a device cannot be used to ensure efficient protection of traumatized skin areas of the body against the risk of soiling or contamination through contact with impure elements, in particular with polluted fluids, not only because the cover sheet is provided with perforations, but mainly because the use of double-sided tape, whether with or without perforations, to ensure fastening of said sheet on the skin, cannot guarantee impermeability between them especially when the covered areas present irregular and/or moving shapes.

One objective of the invention is to remedy the inconveniences of the protection devices that have been proposed until now.

BRIEF SUMMARY OF THE INVENTION

According to the invention, this aim is achieved because of a method according to which a fraction or portion of the sheet is cut out, with shapes and dimensions larger than those of the dressing or the traumatized skin area to be covered. The fraction is cut from a basic or non-dedicated global sheet that is thin, flexible and waterproof, preferably being made of a non-allergenic material and having dimensions which allow cutouts of a number of individually adapted protective fractions or portions. A bead of adhesive that is also waterproof and non-allergenic, having properties which allow it to adhere at the same time to both the skin and the protecting sheet, is placed on the skin in a continuous manner, around the dressing or the traumatized skin area. The portion or fraction of the adapted sheet is finally placed as a protection cover over the dressing or the wounded skin area, so that its edge is applied on the peripheral adhesive bead in order to achieve a close juncture without a discontinuity between the skin and the individually adapted cover sheet and the isolation of the dressing and/or of the wounded skin area.

The protection kit according to the invention comprises a case which holds:
  at least one global or basic, non-dedicated, thin, flexible and waterproof sheet, having dimensions that allow the cutting out of a number of single or individually adapted cover pieces, this global sheet being preferably made of a non-allergenic material that can easily be divided into pieces or fractions of smaller sizes, for example with a pair of scissors; and
  a packaging consisting of a compressible tube containing a water-impermeable and non-allergenic pasty adhesive, being preferably provided with a mouth for dispensing this adhesive in the form of a bead, said adhesive featuring properties which allow it to adhere to the skin as well as to the protection sheet.

It is clear that the protection method and the kit according to the invention provide "made-to-measure", i.e., customizable, protection of dressings or traumatized skin areas of the body (abrasions, scars, insect bites, sunburn . . .). The appearance is generally unforeseen and may involve parts of the body of a great variety of shapes. Furthermore, the protection afforded by the device and the method of the invention provides a guarantee against the risks of soiling or contamination of the protected parts by contact with impure elements, i.e., contaminants, including polluted fluids.

In effect, the deposit of a continuous seam of adhesive between the skin and the protecting sheet allows not only an efficacious attachment of the sheet, the sheet being structured and arranged such that, when applied over the dressing or traumatized area of skin, is non-coated with adhesive, but also ensures the function of a perfectly impermeable barrier. This continuous barrier being placed in direct connection between the skin and the sheet ensures a total peripheral attachment, with no discontinuity and excellent impermeability.

When used for protection of a dressing that has been applied to an area of skin, the components of the kit of the invention can be said to comprise a customizable secondary dressing for such primary dressing.

The protection method and kit according to the invention are also easy and quickly usable. They are also very economical.

BRIEF DESCRIPTION OF THE SEVERAL VIEWS OF THE DRAWINGS

The above aims, characteristics and advantages, and even others, will become more apparent from the following description and the attached drawings.

DETAILED DESCRIPTION OF THE INVENTION

Figure 1:
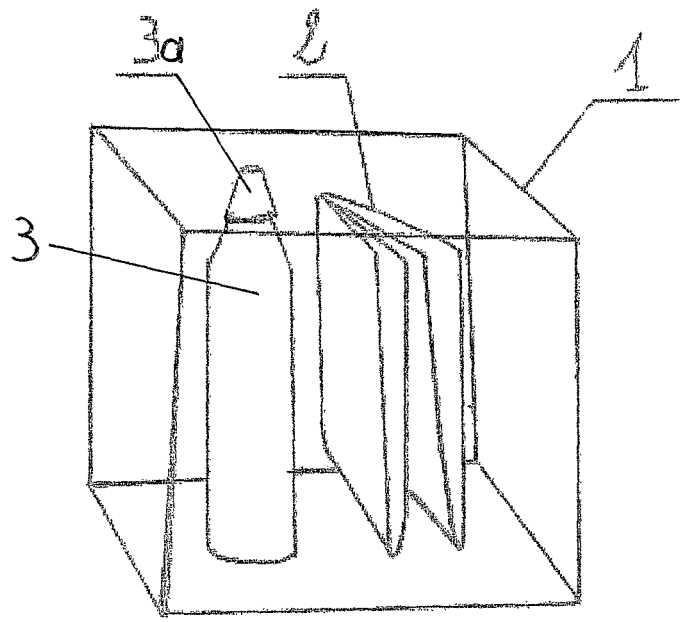
FIG. 1 is a perspective view in the form of a schematic presentation, of a protection kit according to the invention.
Figure 2:
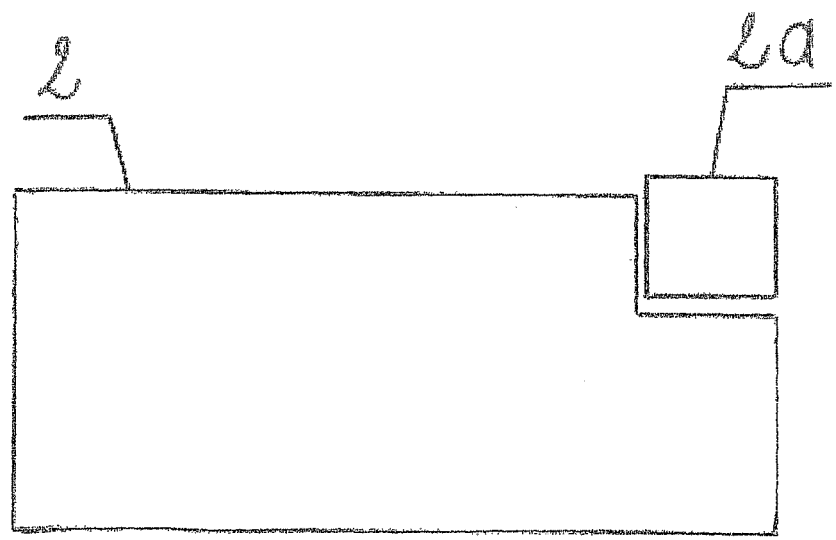
FIG. 2 is a schematic view of an outline sketch showing the cutting of a portion of the individually adapted cover sheet from a non-dedicated basic sheet.

Reference is made to said drawings to describe an interesting example of execution of the protection kit and of the application of the method in accordance with the invention.

The protection kit according to the invention consists essentially of:
a case 1;
at least one flexible, non-dedicated basic or global sheet 2; and
an adhesive container 3.

Case 1 may be made of any material, be of any shape and of any suitable dimensions. The word 'case' has no restrictive character, as this term may designate any analog article such as: a kit, bag, carrying case, box etc. On the other hand, the case 1 maybe equipped with any adequate closing system (zipper, snap button etc.).

The non-dedicated basic or global sheet 2 maybe made of any thin and flexible material, and preferably of a non-allergenic material, for instance of polyurethane or a polyurethane-based polymer that is waterproof and that can easily be cut by means of a hand tool such as a pair of scissors. It features dimensions which allow the cutting of a number of specific individual pieces 2a that are appropriate for covering dressings or wounds of various sizes, shapes and locations. For example, it may have a surface of between 1600 cm$^2$ and 2500 cm$^2$. It may be transparent, translucent, opaque, white or tinted, or even decorated with various printing patterns.

In addition to that, it features advantageously, a thickness of less than 500 μm, for example a thickness between 5 μm and 500 μm and preferably a thickness between 10 μm and 80 μm.

The adhesive container 3 may consist of a compressible tube containing an adhesive of pasty consistency 4. The adhesive contained in the container is water-impermeable and possesses properties which allow it to adhere both to the skin and the plastic protection sheet, without having previously been glued to one or the other of the two surfaces. Of course, any other type of container could be used.

The adhesive 4 is also non-allergenic and biocompatible. It may advantageously consist of a copolymer, preferably silicon-based, for example, glue on a polydimethylsiloxane, with functional groups.

The container 3 includes, preferably, an extruder head or a mouth 3a fitted in a known manner, so as to allow the dispensing of the adhesive 4 contained in said container in the form of a flexible bead 4a.

The sheet 2 and the container of adhesive 3 constitute a plurality of components of the kit which are positioned within the case 1 and which two components are sized and structured for use together in protecting a dressing or an injured area of the skin.

Figure 3:
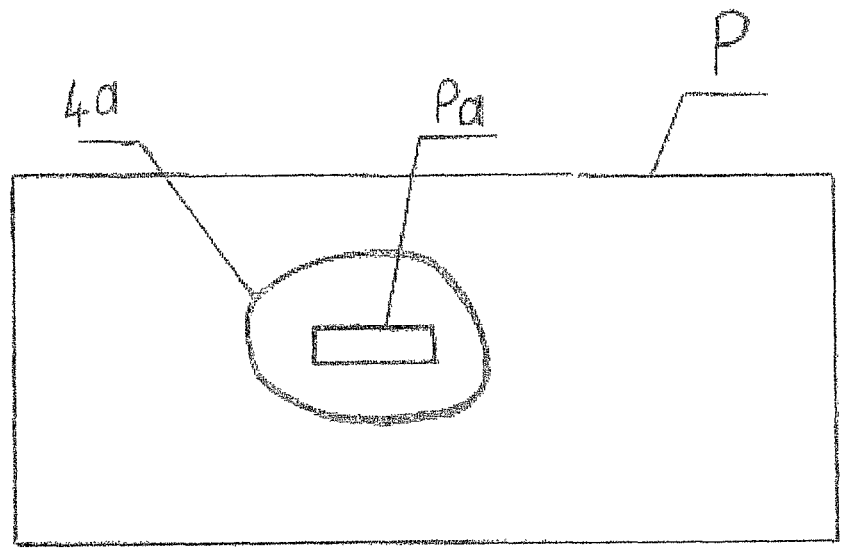
FIG. 3 is a schematic view of an outline sketch at a larger scale, illustrating the application of an adhesive bead on the skin area, around a dressing.
Figure 4:
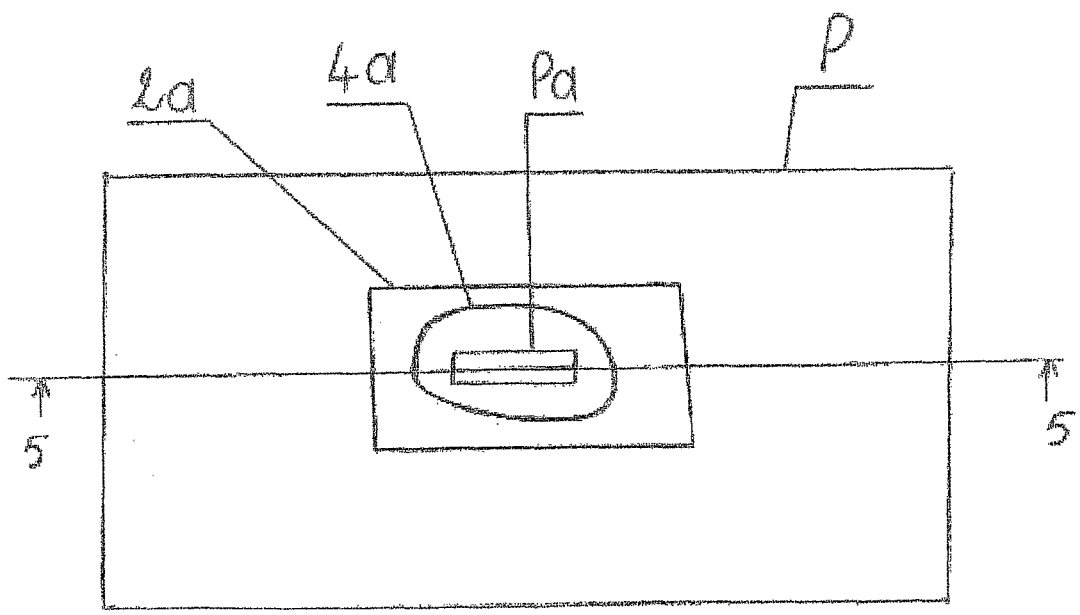
FIG. 4 is a schematic view of an outline sketch showing the application of the cut protection sheet on the deposited adhesive bead, as a cover over the dressing.
Figure 5:
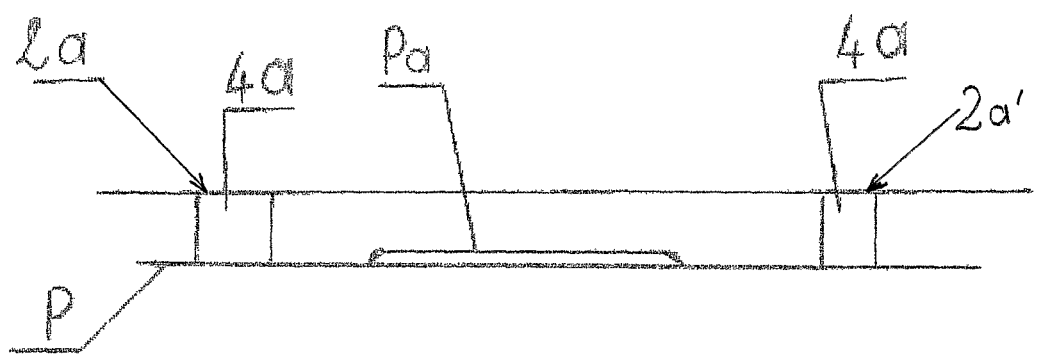
FIG. 5 is a sectional view on a larger scale along line 5-5 of FIG. 4.

According to the method of the invention, a fraction or piece 2a is cut to the desirable dimensions and shape, depending on the size and shape of the dressing or the injured skin area P, from a non-dedicated basic or global sheet 2 that is thin, flexible and waterproof, preferably made of a non-allergenic material and of dimensions suitable to obtain cuttings of a number of individual protecting fractions or portions. A flexible and waterproof non-allergenic adhesive, shown in FIGS. 3-5 as a bead 4a, featuring properties that make it adhere to the skin and to the protection sheet, is deposited on the skin P around the dressing Pa or the traumatized skin area to be protected. The portion or fraction 2a, i.e., the individually adapted sheet, is finally placed as a protection cover over the dressing or of the injured skin area, so that its edge is applied on the peripheral adhesive bead 4a, achieving a close juncture between the skin and the individually adapted protection cover and the isolation of the dressing and/or the injured skin area.

I claim:

1. A kit for protecting at least one of a dressing and a traumatized area of skin of a human body, the kit comprising:
a case having an interior volume;
a plurality of components positioned within said case, said plurality of components being sized and structured for use together in protecting one of a dressing on a traumatized area of skin, said components including at least one sheet and a container of adhesive;
the at least one sheet being flexible and waterproof;
the at least one sheet being of a non-allergenic material;
the at least one sheet having a size and a shape non-dedicated to a size or shape of a dressing having been applied to an area of skin or a size or shape of a traumatized area of skin;
the size and a thickness of the at least one sheet being suitable for being removed from the case and cut into a protection cover having a size that is a fraction of the size of the at least one sheet;
the at least one sheet being non-coated with adhesive on a surface to face the skin;
the protection cover requiring adhesive to be added, after removal of the sheet from the case, to adhere the protection cover relative to the skin;
the adhesive containing a pasty, waterproof, and non-allergenic adhesive, the adhesive being suitable so as to allow adherence to both the skin of the human body, in an area surrounding the dressing, or traumatized area of skin, and to the protection cover;
the container having an extrusion opening structured to facilitate depositing a closed peripheral bead of the adhesive only onto the skin surrounding the dressing or traumatized area and, with the protection cover applied upon the closed peripheral bead of the adhesive, to facilitate placing an impermeable barrier isolating the dressing or traumatized area of skin beneath the protection cover from contaminants.

2. A kit according to claim 1, wherein:
the container comprises a compressible tube.

3. A kit according to claim 2, wherein:
the compressible tube has an extrusion head, said opening being at an end of the extrusion head, to allow dispensing of the adhesive therethrough in a bead form.

4. A kit according to claim 1, wherein:
the at least one sheet comprises a polyurethane material.

5. A kit according to claim 1, wherein:
the at least one sheet comprises a polyurethane-based polymer.

6. A kit according to claim 1, wherein:
the adhesive comprises a copolymer material.

7. A kit according to claim 6, wherein:
the adhesive comprises a silicone-based copolymer.

8. A kit according to claim 7, wherein:
the adhesive comprises a polydimethysiloxane-based glue.

9. A kit according to claim 1, wherein:
the thickness of the sheet is less than 500 μm.

10. A kit according to claim 1, wherein:
the thickness of the at least one sheet is no less than 5 μm.

11. A kit according to claim 1, wherein:
the thickness of the at least one sheet is between 10 μm and 80 μm.

12. A kit according to claim 1, wherein:
the at least one sheet has a surface area of at least 1600 cm$^2$.

13. A kit according to claim 1, wherein:
the at least one sheet has a surface area between 1600 cm$^2$ and 2500 cm$^2$.

14. A kit according to claim 1, wherein:
the at least one sheet is non-coated with adhesive so that the adhesive of the container of adhesive can guarantee impermeability between the protection cover and the skin.

15. A kit according to claim 1, wherein:
the size and a thickness of the at least one sheet is suitable for being removed from the case and cut into one of a plurality of protection covers, each of said plurality being a made-to-measure protection cover having a size dedicated to cover a specific dressing or traumatized skin area.

16. A method of using the kit according to claim 1, comprising:
removing a sheet of the at least one sheet from the case;
cutting the removed sheet into a shape to create a protection cover;
depositing a peripheral bead of the adhesive from the container onto the skin to surround the dressing or traumatized area;
placing the protection cover upon the peripheral bead of adhesive to form a continuous barrier around the dressing or traumatized area skin to isolate the dressing or traumatized area of skin beneath the protection cover from contaminants.

17. A method of using the kit according to claim 16, wherein:
the at least one sheet comprises a polyurethane or a polyurethane-based material.

18. A method of using the kit according to claim 16, wherein:
the adhesive is a copolymer to achieve adhesion and impermeability of the peripheral bead of adhesive.

19. A method of using the kit according to claim 16, wherein:
the adhesive is a silicone-based copolymer to achieve adhesion and impermeability of the peripheral bead of adhesive.

20. A method of using the kit according to claim 19, wherein:
the adhesive consists of a polydimethylsiloxane-based glue.

21. A kit comprising a customizable secondary dressing for a primary dressing of a traumatized area of skin of a human body, the kit comprising:
a case having an interior volume;
a plurality of components positioned within the case, the plurality of components being sized and structured for use together in protecting a primary dressing on a traumatized area of skin, and not contacting the traumatized area of skin, the components comprising:
at least one sheet; and
a container of adhesive;
the at least one sheet being flexible and waterproof;
the at least one sheet being of a non-allergenic material;
the at least one sheet having a size and a shape non-dedicated to a size or shape of the primary dressing on the traumatized area of skin;
the size and a thickness of the at least one sheet being suitable for being removed from the case and cut into a protection cover, the protection cover having a surface area that is a fraction of a surface area of the at least one sheet;
the thickness of the at least one sheet being less than 500 μm;
the at least one sheet being non-coated with adhesive on a surface which is to be affixed facing the skin so that the adhesive from the container of adhesive can be used to guarantee impermeability between the protection cover and the skin;
the adhesive from the container adapted to be affixed to both the skin and to the protection cover to affix the protection cover in relation to the skin ;
the adhesive being a pasty, waterproof, and non-allergenic adhesive, the adhesive being suitable for allowing adherence to an area of the skin surrounding the primary dressing and adherence to the protection cover;
the container having an extrusion opening structured to facilitate depositing a closed peripheral bead of the adhesive onto the area of skin surrounding the primary dressing;
the protection cover and the closed peripheral bead of the adhesive, when the former is secured upon the latter, forming a secondary dressing, the secondary dressing providing a continuous and total peripheral attachment and impermeable barrier around the primary dressing, isolating the primary dressing beneath the protection cover from contaminants.

22. A kit according to claim 21, wherein:
the thickness of the at least one sheet is between 10 μm and 80 μm.

23. A kit according to claim 21, wherein:
the at least one sheet is structured and arranged to be removed from the case and cut into one of a plurality of protection covers, each of the plurality being a customizable protection cover having a size dedicated to cover a respective primary dressing.

* * * * *